US012766259B2

(12) United States Patent
Park et al.

(10) Patent No.: US 12,766,259 B2
(45) Date of Patent: Oct. 20, 2026

(54) BLOOD GLUCOSE CONTROL SYSTEM AND METHOD

(71) Applicants: CURESTREAM CO., LTD., Daegu (KR); POSTECH RESEARCH AND BUSINESS DEVELOPMENT FOUNDATION, Pohang-si (KR)

(72) Inventors: Sung Min Park, Daegu (KR); Gang Wook Kim, Daegu (KR)

(73) Assignees: CURESTREAM CO., LTD., Daegu (KR); POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 742 days.

(21) Appl. No.: 18/027,640

(22) PCT Filed: Oct. 26, 2020

(86) PCT No.: PCT/KR2020/014658
§ 371 (c)(1),
(2) Date: Mar. 22, 2023

(87) PCT Pub. No.: WO2022/065569
PCT Pub. Date: Mar. 31, 2022

(65) Prior Publication Data

US 2023/0381412 A1 Nov. 30, 2023

(30) Foreign Application Priority Data

Sep. 22, 2020 (KR) ........................ 10-2020-0122465

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14244* (2013.01); *A61M 5/16877* (2013.01);
(Continued)

(58) Field of Classification Search
CPC .......... A61M 5/14244; A61M 5/16877; A61M 5/1723; A61M 2230/08; A61M 2205/52; G16H 20/17; G16H 10/60; G16H 50/20
(Continued)

(56) References Cited

U.S. PATENT DOCUMENTS

2005/0171503 A1* 8/2005 Van Den Berghe ......................... A61M 5/1723 604/504
2015/0217052 A1* 8/2015 Keenan .................. G16H 20/17 604/504
(Continued)

FOREIGN PATENT DOCUMENTS

JP 2010-531707 A 9/2010
JP 2017-538474 A 12/2017
(Continued)

OTHER PUBLICATIONS

International Search Report for PCT/KR2020/014658 mailed Jun. 16, 2021 from Korean Intellectual Property Office.

*Primary Examiner* — Philip E Stimpert
(74) *Attorney, Agent, or Firm* — Revolution IP, PLLC

(57) ABSTRACT

A blood glucose control system according to an embodiment of the present invention includes a continuous blood glucose meter configured to continuously measuring blood glucose of a patient, a bio-signal sensor configured to acquire a bio-signal of the patient, a lifelog data collector configured to collect lifelog data of the patient, an insulin injection controller configured to determine an insulin injection amount and an injection rate based on one or more of blood glucose measurement information and blood glucose
(Continued)

metabolism characteristic information received from the continuous blood glucose meter, the bio-signal acquired by the bio-signal sensor or a stress level of the patient indexed by the bio-signal, and the lifelog data collected by the lifelog data collector, and an insulin pump configured to inject insulin into a body of the patient according to the insulin injection amount and the injection rate determined by the insulin injection controller.

9 Claims, 3 Drawing Sheets

(51) Int. Cl.

| | |
|---|---|
| ***A61M 5/168*** | (2006.01) |
| ***G16H 10/60*** | (2018.01) |
| ***G16H 20/17*** | (2018.01) |
| ***G16H 50/20*** | (2018.01) |
| *G16H 20/60* | (2018.01) |
| *G16H 40/67* | (2018.01) |

(52) U.S. Cl.
CPC ............. *G16H 10/60* (2018.01); *G16H 20/17* (2018.01); *G16H 50/20* (2018.01); *A61M 2230/08* (2013.01); *G16H 20/60* (2018.01); *G16H 40/67* (2018.01)

(58) Field of Classification Search
USPC .......................................................... 604/504
See application file for complete search history.

(56) References Cited

U.S. PATENT DOCUMENTS

| | | | | |
|---|---|---|---|---|
| 2017/0215811 | A1* | 8/2017 | Newberry ......... | A61M 5/14248 |
| 2017/0228518 | A1* | 8/2017 | Booth .................. | A61B 5/7475 |
| 2018/0200438 | A1* | 7/2018 | Mazlish .............. | A61M 5/1723 |

FOREIGN PATENT DOCUMENTS

| | | | |
|---|---|---|---|
| KR | 10-2008-0011772 | A | 2/2008 |
| KR | 10-0945735 | B1 | 3/2010 |
| KR | 10-2012-0047841 | A | 5/2012 |
| KR | 10-2013-0135677 | A | 12/2013 |

* cited by examiner

[FIG. 1]
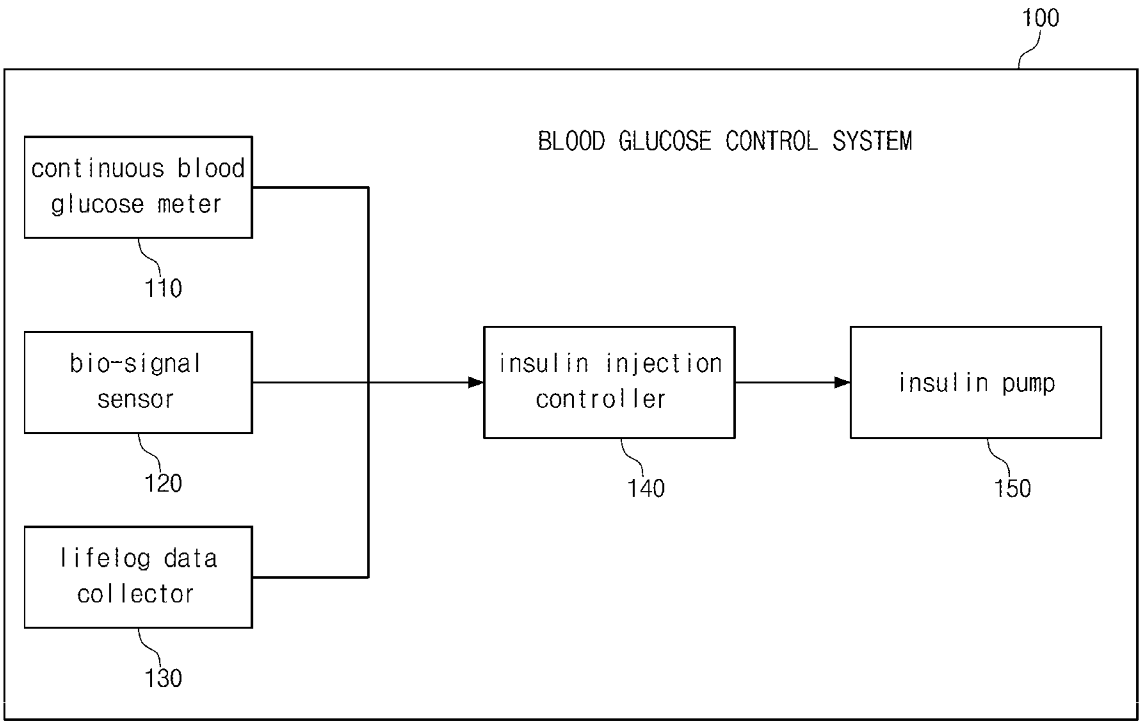

[FIG. 2]
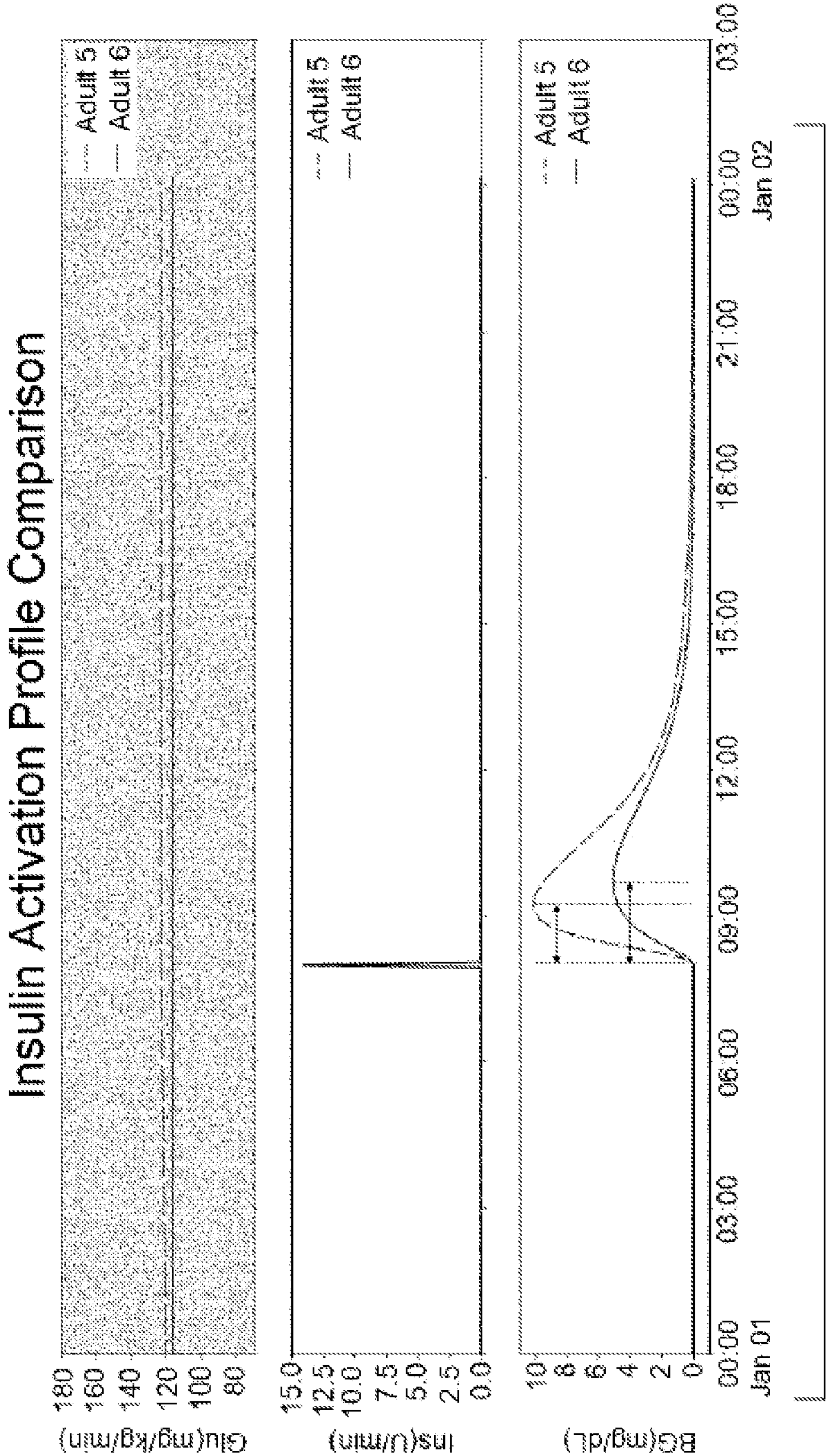

[FIG. 3]
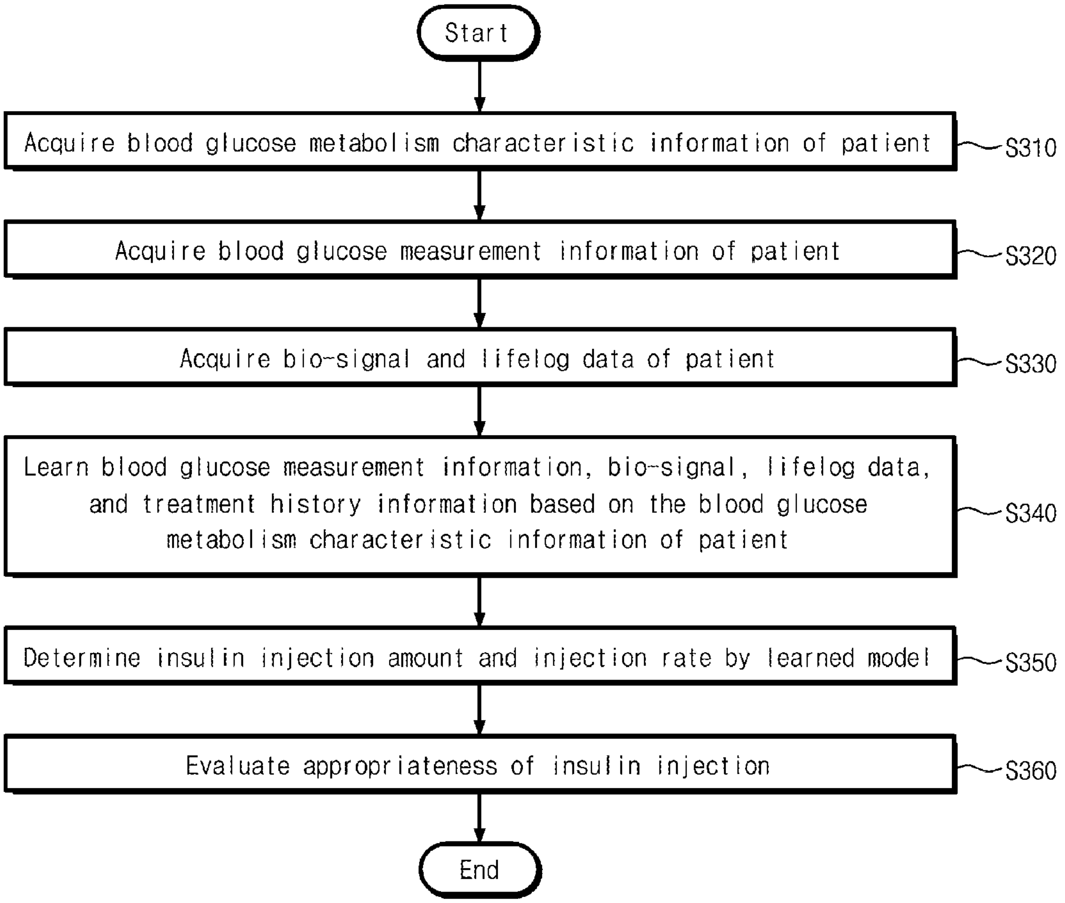

BLOOD GLUCOSE CONTROL SYSTEM AND METHOD

TECHNICAL FIELD

The present invention relates to a blood glucose control system and a blood glucose control method.

BACKGROUND ART

Diabetes is a type of metabolic disease by which insulin secretion is insufficient or normal function is not performed and is characterized in that blood glucose concentration is increased.

A method for treating diabetes includes diet therapy, exercise therapy, drug therapy, insulin injection, and so on, and recently, a method of utilizing an artificial pancreas has been developed.

The artificial pancreas is widely used as an alternative means to overcome limitations of existing treatment methods for diabetic patients who have to rely on insulin.

The artificial pancreas includes a continuous glucose monitoring (CGM), an insulin pump patch, and a control algorithm and is configured to control the insulin pump patch by using values measured in the CGM by the control algorithm.

In general, the control algorithm is configured to control the insulin pump patch to reduce an error between blood glucose of a current or future patient and target blood glucose based on blood glucose information and insulin injection history of the patient.

However, diabetes is greatly affected by significant differences in individual physiological characteristics and individual characteristics changing over time, and furthermore, by individual lifestyles, such as activity, food amount, and sleep, and an individual mental health condition (for example, a stress level), and accordingly, the known static control algorithm that does not reflect this or the known adaptive control algorithms that imperfectly simulate physiological characteristics have limitations, and in particular, a control algorithm that does not consider an individual lifestyle or mental health condition has limitation in responding to a change in blood glucose.

DISCLOSURE

Technical Problem

Accordingly, a current technical art requires a method of controlling blood glucose in consideration of an individual lifestyle and an individual mental health condition.

Technical Solution

In order to solve the above problems, one embodiment of the present invention provides a blood glucose control system.

A blood glucose control system may include a continuous blood glucose meter configured to continuously measuring blood glucose of a patient, a bio-signal sensor configured to acquire a bio-signal of the patient, a lifelog data collector configured to collect lifelog data of the patient, an insulin injection controller configured to determine an insulin injection amount and an injection rate based on one or more of blood glucose measurement information and blood glucose metabolism characteristic information received from the continuous blood glucose meter, the bio-signal acquired by the bio-signal sensor or a stress level of the patient indexed by the bio-signal, and the lifelog data collected by the lifelog data collector, and an insulin pump configured to inject insulin into a body of the patient according to the insulin injection amount and the injection rate determined by the insulin injection controller.

In addition, another embodiment of the present invention provides a blood glucose control method.

The blood glucose control method may include a step of acquiring blood glucose metabolism characteristics information of a patient, a step of acquiring blood glucose measurement information of the patient, a step of acquiring a bio-signal and lifelog data of the patient, a step of learning the blood glucose measurement information, the bio-signal or a stress level of the patient indexed based on the bio-signal, lifelog data, and treatment history information based on the blood glucose metabolism characteristic information, and a step of determining an insulin injection amount and an injection rate by an insulin pump based on a learned model.

In addition, solutions to the above problems do not include all characteristics of the present invention. Various characteristics of the present invention and advantages and effects thereof may be understood in more detail with reference to detailed embodiments below.

Advantageous Effects

According to an embodiment of the present invention, blood glucose may be adjusted in consideration of a lifestyle and a mental health condition of an individual, and through this, a preemptive response to a rapid change in blood glucose may be made.

DESCRIPTION OF DRAWINGS

FIG. 1 is a configuration diagram of a blood glucose control system according to an embodiment of the present invention.

FIG. 2 is a diagram illustrating an example in which insulin activation profiles of an individual are compared with each other.

FIG. 3 is a flowchart of a blood glucose control method according to another embodiment of the present invention.

DESCRIPTION OF REFERENCE NUMBER

100: blood glucose control system
110: continuous blood glucose meter
120: bio-signal sensor
130: lifelog data collector 140
140: insulin injection controller
150: insulin pump

BEST MODE

Hereinafter, preferred embodiments will be described in detail such that those skilled in the art to which the present invention belongs may easily practice the present invention with reference to the accompanying drawings. However, in a case in which it is determined that a detailed description of a related known function or configuration may unnecessarily obscure the gist of the present invention in describing the preferred embodiments of the present invention in detail, the detailed description is omitted. In addition, the same reference numerals are used for parts having similar functions and operations throughout the drawings.

In addition, throughout the specification, when a portion or a unit is described to be "connected" to another portion or another unit, this includes not only a case of being "directly connected", but also a case of being "indirectly connected" with other elements there between. In addition, "including" a certain component means that other components may be further included, rather than excluding other components unless otherwise stated.

FIG. 1 is a block diagram of a blood glucose control system according to an embodiment of the present invention.

Referring to FIG. 1, a blood glucose control system 100 according to an embodiment of the present invention may include a continuous blood glucose meter 110, a bio-signal sensor 120, a lifelog data collector 130, an insulin injection controller 140, and an insulin pump 150.

The continuous blood glucose meter 110 may continuously measure a patient's blood glucose and transmit blood glucose measurement information to the insulin injection controller 140 through wireless communication.

According to one embodiment, the continuous blood glucose meter 110 may be configured to include a sensor for measuring blood glucose and a transceiver for data communication. Here, the sensor may be inserted into a patient's subcutaneous fat to measure glucose in intracellular fluid, and the transceiver may transmit blood glucose measurement information measured by the sensor to the insulin injection controller 140.

The bio-signal sensor 120 may acquire a patient's bio-signal and transmit the bio-signal to the insulin injection controller 140 through wireless communication.

According to one embodiment, the bio-signal sensor 120 may include an electrocardiogram sensor or a heart rate sensor, through which a state of the patient's cardiovascular system may be monitored.

In addition, the bio-signal sensor 120 may include a respiration sensor, through which a state of the patient's respiratory system may be monitored.

According to another embodiment, the bio-signal sensor 120 may further include a processor for analyzing the acquired bio-signal, and the processor may analyze the bio-signal acquired by the electrocardiogram sensor, the heart rate sensor, and the respiration sensor and may index a patient's stress level. Here, various methods known to those skilled in the art may be selectively applied as a method of indexing the patient's stress level, and detailed descriptions thereof are omitted.

The bio-signal sensor 120 described above may be implemented in the form of a wearable sensor that may be worn by a patient. Accordingly, the patient may wear the bio-signal sensor 120 in daily life to periodically acquire the patient's bio-signal at a preset time and reflect the bio-signal in insulin injection control.

The lifelog data collector 130 may collect lifelog data including physical activation information, meal information, sleep information, and so on of a patient, and transmit the lifelog data to the insulin injection controller 140 through wired or wireless communication.

According to one embodiment, the lifelog data collector 130 may collect the patient's physical activation information (for example, activation amount information and so on) measured by an activation tracker in conjunction with an activation tracker worn by the patient.

In addition, the lifelog data collector 130 may collect meal information (for example, amount of meal, ingested calories, and so on) input by a patient in conjunction with, for example, a meal management application installed on a mobile terminal of the patient.

In addition, the lifelog data collector 130 may collect a patient's sleep information (for example, a sleep pattern, quality of sleep quality, and so on) measured by a sleep sensor and analyzed thereby in conjunction with, for example, the sleep sensor worn by the patient or the sleep sensor arranged near a sleeping patient (for example, on a bed or so on).

The insulin injection controller 140 may determine an insulin injection amount and an injection rate by using the insulin pump 150 based on one or more of blood glucose measurement information received from the continuous blood glucose meter 110, blood glucose metabolism characteristic information of a patient, a bio-signal acquired by the bio-signal sensor 120 or a patient's stress level indexed by the bio-signal, and lifelog data collected by lifelog data collector 130.

Blood glucose regulating hormone greatly changes depending on the type and an action target thereof. Therefore, according to an embodiment of the present invention, the insulin pump 150 may be configured to be controlled in consideration of pieces of blood glucose metabolism characteristic information different from each other for each patient.

In addition, blood glucose is greatly influenced by a patient's lifestyle, such as physical activation, meal, and sleep, and a mental health condition, such as a stress level. Therefore, according to an embodiment of the present invention, it is possible to more precisely determine an insulin injection amount by reflecting an individual's biological situation or activation by additionally considering At least one of lifelog data including the patient's physical activation information, meal information, and sleep information, the patient's bio-signal, and the patient's stress level indexed based on the bio-signal in order to determine in real time the insulin injection amount and an injection rate.

According to an example, the insulin injection controller 140 may receive information on an insulin activation curve or an insulin activation peak time acquired through a preliminary test. Here, a method of acquiring the insulin activation curve will be described with reference to FIG. 2.

For example, insulin activation of a diabetic patient of a first type may be measured through a following glucose clamp test.

1. Basal insulin is continuously injected such that blood glucose of a fasting patient may be maintained constant.
2. A predetermined amount of insulin (for example, 0.2 unit per unit weight) is injected into hypoderm of a patient once (bolus).
3. When a patient's blood glucose is reduced due to the injected insulin, a glucose solution is continuously injected into vein of the patient by the amount of the blood glucose that is reduced to maintain the blood glucose constant.

An injection rate curve of the glucose solution that is injected into vein described in item 3 above is an insulin activation curve.

FIG. 2 is a diagram illustrating an example in which individual insulin activation profiles are compared with each other, and illustrates insulin activation curves measured through a glucose clamp test conducted on two virtual patients having similar weights.

Here, the two virtual patients Adult5 and Adult6 that respectively weigh 67.5 kg and 67.1 kg were injected with the same amount of insulin (14 Units) (see a second graph).

A third graph is an injection rate curve of a glucose solution, which is an insulin activation curve.

Referring to FIG. 2, despite that the same amount of insulin was injected into two patients having similar weights, insulin of Adult5 was most activated after 75 minutes, and insulin of Adult6 was most activated after 102 minutes, and thus, it may be seen that there is a difference of about 30 minutes between the two patients at the time when insulin is most activated, that is, at the peak of insulin activity. That is, at the peak time of insulin activation. This is one example, and the insulin activation peak times may differ from each other by one hour or more depending on patients.

Therefore, according to an embodiment of the present invention, blood glucose control may be optimized for each individual by considering an individual's insulin activation.

According to another embodiment, the insulin injection controller 140 may acquire information on an insulin activation curve or an insulin activation peak time by learning past treatment history information and past blood glucose information of a patient. Here, the treatment history information of the patient may include previous insulin injection information (injection time and injection amount).

According to another embodiment, the insulin injection controller 140 may acquire information on an insulin activation curve or an insulin activation peak time by learning treatment history information and blood glucose information of a patient undergoing insulin treatment.

Meanwhile, the insulin injection controller 140 may continuously update a blood glucose control algorithm by learning blood glucose measurement information received from the continuous blood glucose meter 110, a bio-signal received from the bio-signal sensor 120 or a patient's stress level indexed based on the bio-signal, lifelog data received from the lifelog data collector 130, and a patient's past or current treatment history information, based on the acquired blood glucose metabolism characteristic information of a patient as described above.

First, the insulin injection controller 140 may derive additional information to be described below based on the information input as described above and use the additional information to control the insulin pump 150.

Specifically, when receiving the insulin activation peak time information, the insulin injection controller 140 may obtain an insulin activation curve therefrom.

In addition, the insulin injection controller 140 may acquire an hourly blood glucose change amount from the blood glucose measurement information received from the continuous blood glucose meter 110, that is, the current blood glucose.

In addition, the insulin injection controller 140 may calculate the amount of remaining insulin that is not activated in a patient's body based on the insulin activation curve and the patient's treatment history information.

In addition, the insulin injection controller 140 may check variability of the insulin injection amount based on the patient's treatment history information.

In addition, the insulin injection controller 140 may predict the amount of blood glucose consumption from the lifelog data by additionally considering the amount of activation and may predict the amount of change in blood glucose by additionally considering one or more of the amount of food and the amount of sleep.

Thereafter, the insulin injection controller 140 may learn information on the amount of change in blood glucose over time, the amount of remaining insulin, and variability of the insulin injection amount based on the insulin activation curve and may additionally learn information on the predicted amount of blood glucose consumption and the predicted amount of change in blood glucose based on the lifelog data, and furthermore, may learn information on a bio-signal received from the bio-signal sensor 120 or a patient's stress level indexed based on the bio-signal. The insulin injection amount and an injection rate may be determined by the insulin pump 150 based on the learned model. Here, deep reinforcement learning may be applied for learning.

In this way, according to an embodiment of the present invention, the amount of blood glucose consumption and the amount of change in blood glucose may be predicted based on a patient's lifelog data, and an insulin injection amount and an injection rate may be determined by additionally considering the amounts, and thus, it is possible to preemptively respond to a rapid blood glucose change, such as hypoglycemia or hyperglycemia. In addition, by determining the insulin injection amount and the injection rate by additionally considering a patient's mental health state, an effect of the patient's mental health state on blood glucose control may be considered.

In addition, the insulin injection controller 140 performs learning as described above by using treatment history information and blood glucose information of a patient undergoing insulin treatment, thereby reflecting an individual's physiological characteristics that change over time to update a learned model, and thus, a blood glucose control algorithm may be continuously updated.

Additionally, the insulin injection controller 140 may evaluate whether or not the insulin previously injected is appropriate and reflect the evaluation in future learning.

According to one embodiment, the insulin injection controller 140 may provide compensation according to a degree of maintenance of blood glucose at preset time intervals from the time when the insulin pump 150 injects insulin, that is, compensation according to how well the blood glucose is maintained, and may store the compensation for each time. In this case, the insulin injection controller 140 may assign different weights to compensation for each time according to a patient's insulin activation curve. For example, the weight may be set to zero immediately after insulin injection, and the greatest weight may be assigned to an insulin activation peak time of the insulin activity curve. Thereafter, the insulin injection controller 140 may evaluate whether the insulin injection is appropriate by summing compensations (that is, compensation*weight) in consideration of weights for each time during a preset time (for example, 8 hours) from the time when insulin is injected.

In this way, the insulin injection controller 140 may evaluate appropriateness of insulin injection for each insulin injection performed by the insulin pump 150 and reflect the result of evaluation in a learning algorithm.

The insulin pump 150 may inject insulin into a patient's body according to the insulin injection amount and the injection rate determined by the insulin injection controller 140.

According to the embodiment of the present invention described above, in order to control insulin injection, not only a patient's past condition including information on one of both insulin activation and a treatment history of a patient and information on blood glucose of the patient but also data in which a patient's bio-signal or a patient's current condition including lifelog data are collectively considered, and thus, insulin injection may be controlled more precisely and accurately.

FIG. 3 is a flowchart of a blood glucose control method according to another embodiment of the present invention.

Referring to FIG. 3, first, blood glucose metabolism characteristic information of a patient may be obtained (S310). Here, the blood glucose metabolism characteristic information may include information on an insulin activation curve or an insulin activation peak time.

Thereafter, blood glucose measurement information of the patient may be acquired (S320). Here, the blood glucose measurement information of the patient may be continuously measured by a continuous blood glucose meter.

Thereafter, bio-signal and lifelog data of the patient may be acquired (S330). Here, the bio-signal of the patient may be acquired by an electrocardiogram sensor, a heart rate sensor, and/or a respiration sensor, and the lifelog data of the patient may include physical activation information, meal information, and sleep information of the patient.

Thereafter, blood glucose measurement information, bio-signal or indexed stress level of a patient, lifelog data, and treatment history information may be learned based on the blood glucose metabolism characteristic information of the patient (S340), and an insulin injection amount and an injection rate may be determined by an injection pump based on a learned model (S350).

Then, appropriateness of insulin injection performed by the insulin pump may be evaluated (S360).

The blood glucose control method illustrated in FIG. 3 may be performed by a controller including a learning engine.

In addition, details of each step described above are the same as details described above with reference to FIG. 1, and accordingly, redundant descriptions thereof are omitted.

The present invention is not limited by the above-described embodiments and accompanying drawings. Those skilled in the art to which the present invention belongs may clearly understand that components according to the present invention may be substituted, modified, and changed without departing from the technical idea of the present invention.

The invention claimed is:

1. A blood glucose control system comprising:

a continuous blood glucose meter configured to continuously measure blood glucose of a patient;

a bio-signal sensor configured to acquire a bio-signal of the patient;

a lifelog data collector configured to collect lifelog data of the patient;

an insulin injection controller configured to, obtain an insulin activation curve from insulin activation peak time information of the patient;

obtain a time-based blood glucose change amount from blood glucose measurement information of the patient;

calculate, based on the insulin activation curve and treatment history information of the patient, an amount of remaining insulin that is not activated in the patient's body;

determine, based on the patient's treatment history information, a variability of an insulin injection amount;

predict an amount of blood glucose consumption from the lifelog data of the patient by considering an amount of physical activation of the patient;

predict an amount of change in blood glucose by considering one or more of an amount of food and an amount of sleep of the patient;

learn information on the time-based blood glucose change amount, the amount of remaining insulin, and the variability of the insulin injection amount, based on the insulin activation curve;

learn information on the predicted amount of blood glucose consumption and the predicted amount of change in blood glucose, based on the lifelog data;

learn information on the bio-signal of the patient or a stress level of the patient indexed based on the bio-signal, and determine the insulin injection amount and an injection rate based on a learned model; and an insulin pump configured to inject insulin into a body of the patient according to the insulin injection amount and the injection rate determined by the insulin injection controller.

2. The blood glucose control system of claim 1, wherein the bio-signal sensor includes one of an electrocardiogram sensor and a heart rate sensor and monitors a state of a cardiovascular system of the patient.

3. The blood glucose control system of claim 2, wherein the bio-signal sensor includes a respiration sensor and monitors a state of a respiratory system of the patient.

4. The blood glucose control system of claim 3, wherein the bio-signal sensor includes a processor and analyzes the bio-signal of the patient by using the processor to index the stress level of the patient.

5. The blood glucose control system of claim 1, wherein the lifelog data collector collects physical activation information of the patient measured by an activation tracker in conjunction with the activation tracker worn by the patient.

6. The blood glucose control system of claim 1, wherein the lifelog data collector collects meal information input by the patient in conjunction with a meal management application installed on a portable terminal of the patient.

7. The blood glucose control system of claim 1, wherein the lifelog data collector collects sleep information of the patient measured and analyzed by a sleep sensor in conjunction with the sleep sensor worn by the patient or the sleep sensor arranged near a sleeping patient.

8. A blood glucose control method comprising:

a step of receiving insulin activation peak time information of a patient and obtaining an insulin activation curve from the insulin activation peak time information;

a step of acquiring blood glucose measurement information of the patient and deriving a time-based blood glucose change amount from the blood glucose measurement information;

a step of calculating, based on the insulin activation curve and treatment history information of the patient, an amount of remaining insulin that is not activated in the patient's body;

a step of determining, based on the patient's treatment history information, a variability of an insulin injection amount;

a step of predicting an amount of blood glucose consumption from lifelog data of the patient by considering an amount of physical activation of the patient;

a step of predicting an amount of change in blood glucose by considering one or more of an amount of food and an amount of sleep of the patient;

a step of learning information on the time-based blood glucose change amount, the amount of remaining insulin, and the variability of the insulin injection amount, based on the insulin activation curve, and information on the predicted amount of blood glucose consumption and the predicted amount of change in blood glucose, based on the lifelog data, and information on a bio-signal of the patient or a stress level of the patient indexed based on the bio-signal, to update a learned model; and a step of determining, by an insulin pump, the insulin injection amount and an injection rate based on the learned model.

9. The blood glucose control method of claim 8, further comprising:

a step of evaluating appropriateness of insulin injection by the insulin pump.

* * * * *